United States Patent
Yoshikawa et al.

(10) Patent No.: US 8,911,372 B2
(45) Date of Patent: *Dec. 16, 2014

(54) ULTRASONIC MEDICAL DIAGNOSTIC DEVICE FOR IMAGING CHANGES WITH TIME

(71) Applicant: Hitachi Medical Corporation, Tokyo (JP)

(72) Inventors: Hideki Yoshikawa, Kokubunji (JP); Takashi Azuma, Kodaira (JP); Kenichi Kawabata, Kodaira (JP); Kazuaki Sasaki, Kawasaki (JP); Shinichiro Umemura, Sendai (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/903,287

(22) Filed: May 28, 2013

(65) Prior Publication Data

US 2013/0261451 A1    Oct. 3, 2013

Related U.S. Application Data

(63) Continuation of application No. 11/914,962, filed as application No. PCT/JP2006/309939 on May 18, 2006, now Pat. No. 8,460,191.

(30) Foreign Application Priority Data

May 20, 2005  (JP) .................................. 2005-147485

(51) Int. Cl.
| | | |
|---|---|---|
| A61B 8/00 | (2006.01) | |
| A61B 8/08 | (2006.01) | |
| G06T 5/50 | (2006.01) | |
| G06T 7/20 | (2006.01) | |
| A61B 5/11 | (2006.01) | |

(52) U.S. Cl.
CPC .................. *A61B 8/5207* (2013.01); *A61B 8/08* (2013.01); *G06T 5/50* (2013.01); *G06T 7/2013* (2013.01); *A61B 8/461* (2013.01); *A61B 5/11* (2013.01); *G06T 2207/10132* (2013.01); *G06T 2207/30101* (2013.01)
USPC ........... 600/437; 600/443; 600/453; 600/455; 600/458

(58) Field of Classification Search
USPC .................. 600/407, 437, 443, 453, 455, 458
See application file for complete search history.

(56) References Cited

U.S. PATENT DOCUMENTS

| | | | |
|---|---|---|---|
| 5,048,103 | A | 9/1991 | Leclerc et al. |
| 5,495,846 | A | 3/1996 | Uehara et al. |

(Continued)

FOREIGN PATENT DOCUMENTS

| | | |
|---|---|---|
| JP | 5-38340 | 2/1993 |
| JP | 50-38340 | 2/1993 |

(Continued)

OTHER PUBLICATIONS

European Search Report dated Apr. 16, 2010, issued in European Patent Application No. 06746614.

(Continued)

*Primary Examiner* — James Kish
(74) *Attorney, Agent, or Firm* — Antonelli, Terry, Stout & Kraus, LLP.

(57) ABSTRACT

A diagnostic imaging apparatus for imaging information changing with time and displaying it in real time, composed of an ultrasonic probe (2), having piezoelectric elements arranged in an array form that transmit ultrasonic waves to a target object (1) and acquires a reflection signal from the target object; a body movement measuring unit (12) that constitutes a two-dimensional ultrasonic image using the reflection signal acquired by the ultrasonic probe, sets, in the image plane, a plurality of measuring areas used for measuring the body movement of the target object, and measures the body movement and deformation amounts in the measuring areas; and an image accumulating (subtracting) unit for accumulating or subtracting images using body movement measured by the body movement measurement unit.

6 Claims, 12 Drawing Sheets

(56) References Cited

U.S. PATENT DOCUMENTS

| | | | |
|---|---|---|---|
| 5,503,153 | A | 4/1996 | Liu et al. |
| 5,833,613 | A | 11/1998 | Averkiou et al. |
| 6,095,980 | A | 8/2000 | Burns et al. |
| 6,607,490 | B2 | 8/2003 | Ogasawara et al. |
| 6,620,103 | B1 | 9/2003 | Bruce et al. |

FOREIGN PATENT DOCUMENTS

| | | |
|---|---|---|
| JP | 5-220138 | 8/1993 |
| JP | 8-307771 | 11/1996 |
| JP | 11-26489 | 9/1999 |
| JP | 2001-157677 | 6/2001 |
| JP | 2002-85409 | 3/2002 |
| JP | 2002-209898 | 7/2002 |
| WO | WO 00/57361 A1 | 9/2000 |
| WO | WO2005/074805 * | 8/2005 ............... A61B 8/00 |

OTHER PUBLICATIONS

Chinese Office Action issued in corresponding Chinese Patent Application No. 200680017585.1, dated Sep. 25, 2009.

* cited by examiner

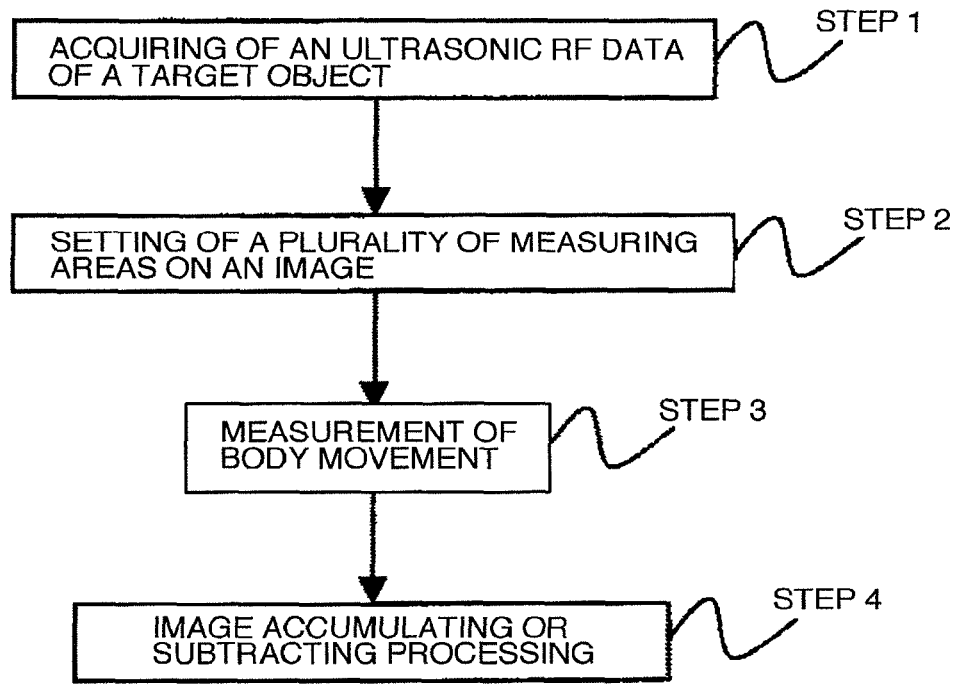
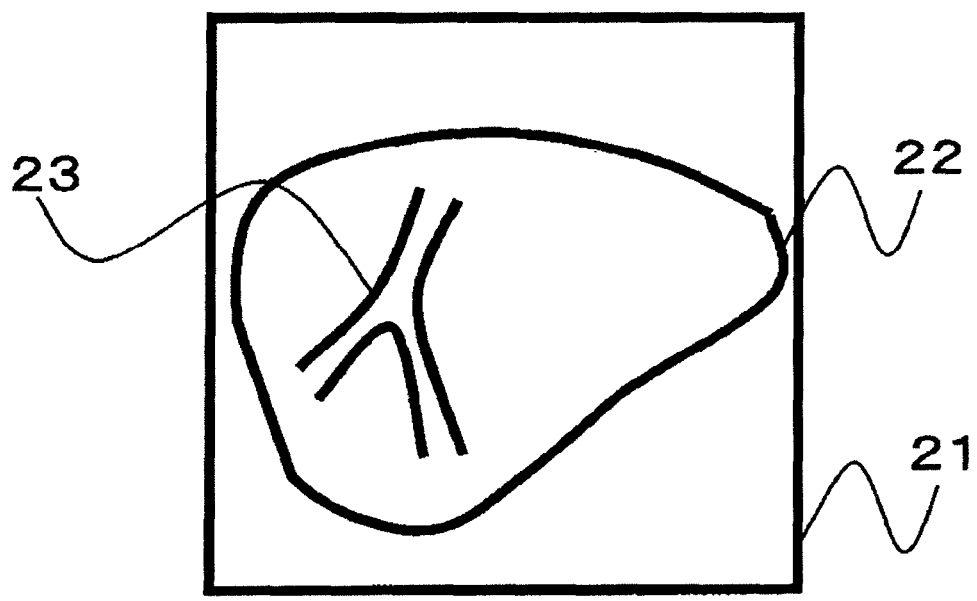

ULTRASONIC MEDICAL DIAGNOSTIC DEVICE FOR IMAGING CHANGES WITH TIME

INCORPORATION BY REFERENCE

The present application is a continuation of U.S. application Ser. No. 11/914,962, now U.S. Pat. No. 8,460,191 that claims priority from Japanese application JP 2005-147485 filed on May 20, 2005, the content of which are hereby incorporated by reference into this application. Application Ser. No. 11/914,962 is a 371 of International Application No. PCT/JP2006/309939, filed on May 18, 2006, now expired.

TECHNICAL FIELD

The present invention relates to a diagnostic imaging apparatus for imaging and displaying information changing with time, by measuring deformation of a target object using ultrasonic waves, and by accumulating or subtracting processing of a plurality of images added correction processing of body movement.

BACKGROUND ART

Technology for extracting and imaging form or tissue degeneration with time of a target object, by using images with different time phases, is useful in therapy effect judgment or lesion discrimination or the like. For example, by correctly extracting and imaging cancer sizes before and after drug dosage, therapy effect of a drug can be judged at an early stage. In addition, use of the technology as a monitoring tool for less invasive therapy, wherein therapy sites cannot be viewed directly, is capable of detecting tissue change of target areas in high sensitivity, and providing therapy not to invade normal sites. Usually, change of a target object with time is judged by an operator, by comparative viewing of images or by superimposing images themselves to be compared, based on characteristic sites such as a skeleton or the like.

Use of time-series images is also capable of extracting a blood vessel structure by tracking movement of an ultrasonic contrast medium. The ultrasonic contrast medium is a minute air bubble with a diameter of about several pms, and irradiation of ultrasonic waves generates a strong nonlinear signal. Because the ultrasonic contrast medium administered from a vein infiltrates into a fine blood vessel with blood flow, a high contrast image can be obtained, wherein a blood vessel structure is highlighted. However, because concentration of the ultrasonic contrast medium is lowered in a blood vessel at a peripheral part, a signal with sufficient S/N ratio (ratio of a signal to noise) cannot be obtained. In addition, at deep areas, reduction of sound pressure of irradiated ultrasonic beams, or fading of a nonlinear signal from the contrast medium also reduces S/N ratio and weakens contrast. Therefore, an operator tracks flow of the ultrasonic contrast medium by eye and judges a blood vessel structure in his (her) head. As a tool to solve a problem of decrease in S/N ratio at deep areas, a method for dividing imaging areas in a depth direction has been proposed (JP-A-2002-209898). Because of irradiation of ultrasonic waves in sound pressure sufficient to obtain a contrast medium signal, for each of the areas with different depth, dispersion of irradiated sound pressure in a depth direction can be reduced. By joining up each of the images acquired, an image, wherein high S/N ratio is maintained, can be obtained even in deep areas.

According to a pulse inversion mode (U.S. Pat. No. 6,095, 980), it has been disclosed that measurement of body movement by cross-correlation calculation using an RF data, and accumulation of images are possible, even in the case where change of a contrast medium signal is large. A pulse inversion mode is a method for acquiring higher harmonic wave components in high S/N ratio, by continuous irradiation of a fundamental wave and a reversed phase wave, and accumulating reflecting waves of both. For example, in the case where a fundamental wave, $f_0=re^{i\theta}$, and a wave having a reversed phase thereto, $f_1=re^{i(\theta-n)}$, are irradiated, each of the reflecting waves thereof contains, in addition to waves of fundamental frequency components, $f_0{}^{re}=re^{i\theta}$, and $f_1{}^{re}=re^{i(\theta-n)}$, high frequency wave components, $f_0{}^{re2}=re^{i2\theta}$, and $f_1{}^{re2}=re^{i2(\theta-n)}$. By subjecting these to accumulating processing, fundamental frequency components disappear, and higher harmonic wave components double. On the other hand, by subjecting these to subtracting processing, only fundamental frequency components are left, and high frequency wave components disappear.

DISCLOSURE OF THE INVENTION

To detect change of a target object with time, images themselves obtained at different time phases should be compared. Therefore, a method for measuring and correcting displacement or deformation of a target object (hereafter referred to as body movement, as a collective term) is inevitable. Technology described in JP-A-2002-209898 extracts a blood vessel structure having a diameter of about several mms, which thus makes difficult to draw a blood vessel structure without correct measurement and correction, even for body movement of about 1 mm.

Therefore, it is an object of the present invention to provide a diagnostic imaging apparatus for extracting and imaging information changing with time, from time-series images obtained in different time phases, by a method for measuring and correcting body movement of a target object.

To attain the above object, in a diagnostic imaging apparatus of the present invention, information changing with time such as form or tissue degeneration of a target object is imaged and displayed, by measuring body movement in an imaging plane of a target object using ultrasonic images, and while adding correction processing of body movement amount measured, by accumulating or subtracting time-series images.

Typical constitution examples of a diagnostic imaging apparatus of the present invention will be listed below.

(1) A diagnostic imaging apparatus having an ultrasonic probe for transmitting ultrasonic waves to a target object, and acquiring a reflection signal from the target object; a body movement measuring unit that constitutes two-dimensional ultrasonic images using the reflection signal acquired by the ultrasonic probe, sets, in the image plane, a plurality of measuring areas for measuring the body movement of the target object, and measures the body movement in the measuring areas; an image accumulating (subtracting) unit for carrying out accumulating or subtracting processing of images by correcting body movement measured in the body movement measurement unit, to extract information changing with time; and an image display unit for displaying images acquired in the image accumulating (subtracting) unit.

(2) The diagnostic imaging apparatus of the above (1), characterized in that the body movement measuring unit sets a plurality of measuring areas for measuring the body movement, in a plane of the two-dimensional ultrasonic images acquired by transmitting and receiving ultrasonic waves, and measures body movement in the measuring areas.

(3) The diagnostic imaging apparatus of the above (1), characterized in that the ultrasonic probe for transmitting and receiving ultrasonic signals is an ultrasonic probe having each of a plurality of piezoelectric elements arranged in a one-dimensional or two-dimensional array form.

(4) The diagnostic imaging apparatus of the above (1), characterized in that a plurality pieces of images with different time phases are subjected to accumulating or subtracting processing, and thus information changing with time, on such as form or tissue degeneration of a target areas, is imaged.

(5) The diagnostic imaging apparatus of the above (4), characterized in that the images used in accumulating or subtracting processing are morphology images such as ultrasonic images, MRI images, or X-ray images, or functional images such as PET images, or ultrasonic contrast medium images.

(6) A diagnostic imaging apparatus characterized by being provided with an ultrasonic probe for transmitting and receiving ultrasonic waves to and from a target object, and acquiring two-dimensional tomographic images of the target object; a unit for measuring body movement of a target object from ultrasonic images acquired by the ultrasonic probe; a unit for subjecting time-series images to accumulating or subtracting processing by correcting body movement measured; and an image display unit for displaying images acquired by the accumulating or subtracting processing.

According to the present invention, it is possible to image information, which can be known only by plurality pieces of time-series images, such as tissue form change or flow of a contrast medium, and also to display conventionally abstract and qualitative information, as specifically and commonly sharable images among doctors themselves, or between a doctor and a patient.

Other objects, features and advantages of the present invention will be made clear with reference to the following description of embodiments of the present invention on accompanying drawings.

BRIEF DESCRIPTION OF THE DRAWINGS

FIG. 2 is a flow chart explaining action from RF data acquiring to image accumulating or subtracting processing, in a diagnostic imaging apparatus of the embodiment.

FIG. 3A is a drawing showing setting of a plurality of measuring areas, in a diagnostic imaging apparatus of the embodiment.

EMBODIMENTS

Detailed description will be given below on embodiments of the present invention with reference to drawings.

Figure 1:
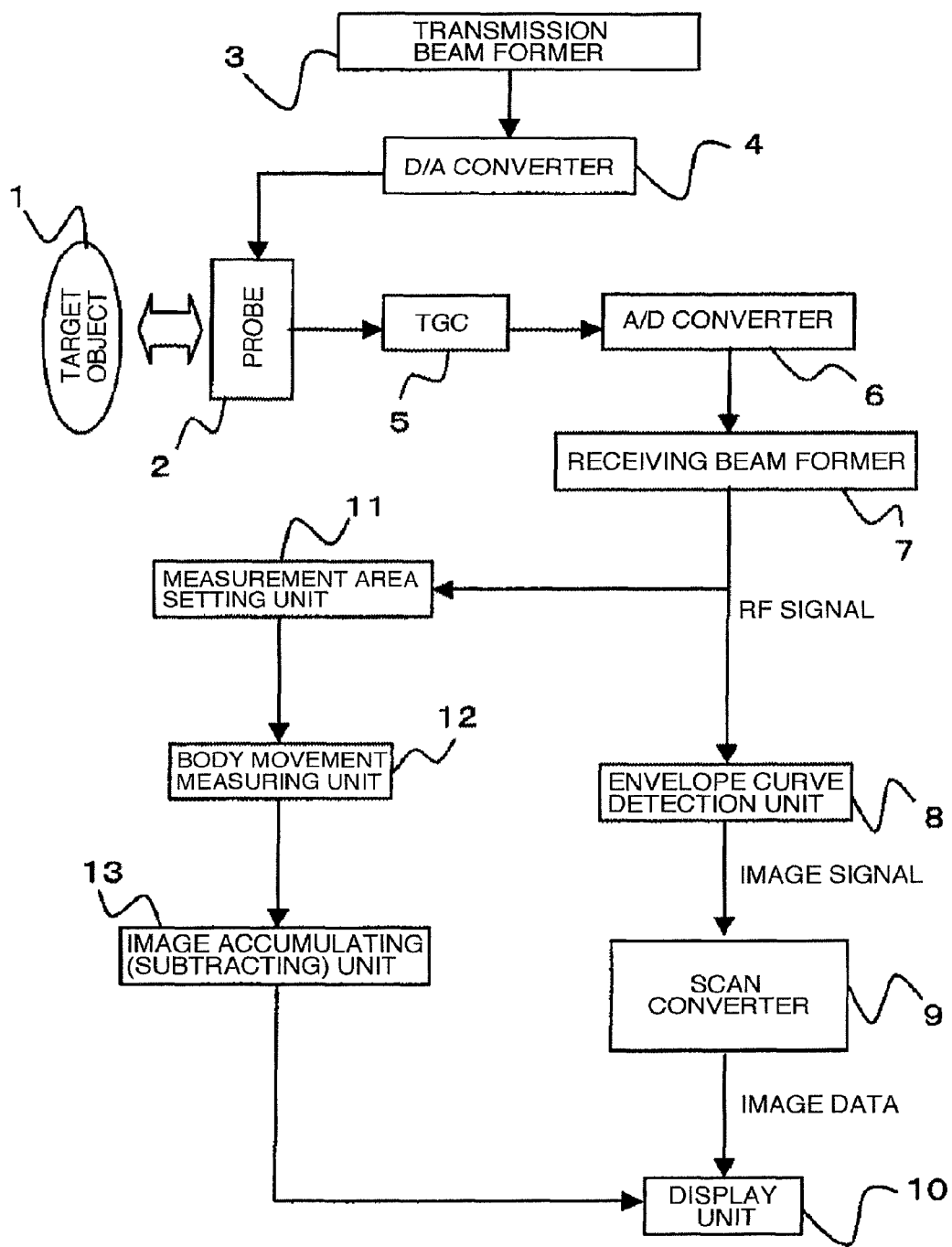
FIG. 1 is a block diagram showing a configuration of a diagnostic imaging apparatus according to the embodiment of present invention.

FIG. 1 is a block diagram showing a constitution of a diagnostic imaging apparatus according to one embodiment of the present invention. In the diagnostic imaging apparatus of the present invention, a two-dimensional tomographic image (a B mode image) is acquired by transmitting and receiving ultrasonic waves to and from a target object, and the two-dimensional tomographic image is divided into a plurality of measurement areas to measure body movement in the measurement areas. Then plurality pieces of images are accumulated or subtracted to display a re-constituted two-dimensional image using the divided measurement areas.

First, explanation will be given on apparatus configuration from acquiring ultrasonic images of a target object to displaying accumulated or subtracted images added body movement correction, with reference to a block diagram of FIG. 1. The ultrasonic probe (hereafter a probe) 2 has a structure where a plurality of piezoelectric elements are arranged. An analogue wave signal is transmitted from the transmission beam former 3 to each of the piezoelectric elements via the D/A converter 4, and ultrasonic waves are irradiated toward the target object 1. The ultrasonic waves transmitted from each of the piezoelectric elements are introduced with an electronic delay by the transmission beam former 3, and focused at a predetermined depth. The transmitted wave signal is reflected inside the target object 1, and received again by each of the piezoelectric elements of the probe. A reflection echo received by each of the piezoelectric elements is corrected by decayed amount, which changes depending on arrival depth of a transmitted wave, by the TGC (Time Gain Control) unit 5, and subsequently converted to a digital signal by the A/D converter 6, and sent to the receiving beam former 7.

At the receiving beam former 7, accumulation result is output by being introduced with a delay time corresponding to distance from a focus position to each of the piezoelectric elements. By subjecting this focused ultrasonic wave to two-dimensional scanning, a two-dimensional reflecting echo distribution of the target object 1 is obtained. From the receiving beam former 7, an RF signal, which is divided to a real part and an imaginary part, is output, and sent to the envelope curve detection unit 8 and the measurement area setting unit 11. The signal sent to the envelope curve detection unit 8 is converted to a video signal, and subsequently interpolation between scanning lines is added by the scan converter 9, re-constituted to a two-dimensional image data, and then displayed onto the image display unit 10. At the measurement area setting unit 11, measurement areas to measure body movement are set to an optimal size corresponding to a structure, as will be described later, and sent to the body movement measuring unit 12. At the body movement measuring unit 12, body movement inside the measurement areas are measured. A method for measuring body movement is cross-correlation calculation or a least square method. At the image accumulating (subtracting) unit 13, image accumulating or subtracting processing is carried out in the measurement areas, while adding correction based on a speed component vector of body movement measured at the body movement measurement areas, to be displayed onto the display unit 10.

Then, detailed explanation will be given on the steps from acquiring an RF data to displaying, according to a flow chart of FIG. 2. First of all, an ultrasonic RF data is acquired at the step 1. An ultrasonic probe to acquire images is classified into a one-dimensional array type and a two-dimensional array type. The two-dimensional array type is capable of imaging an arbitrary cross-section, which therefore determines tree-dimensional body movement of a target object, by acquiring an image data in a direction orthogonal to a target imaging plane, and by measuring body movement in the image data. By changing the target imaging plane corresponding to the measurement results, imaging of the same area at all times, and accumulating or subtraction processing, without being influenced by movement of a target object, are possible.

Figure 3B:
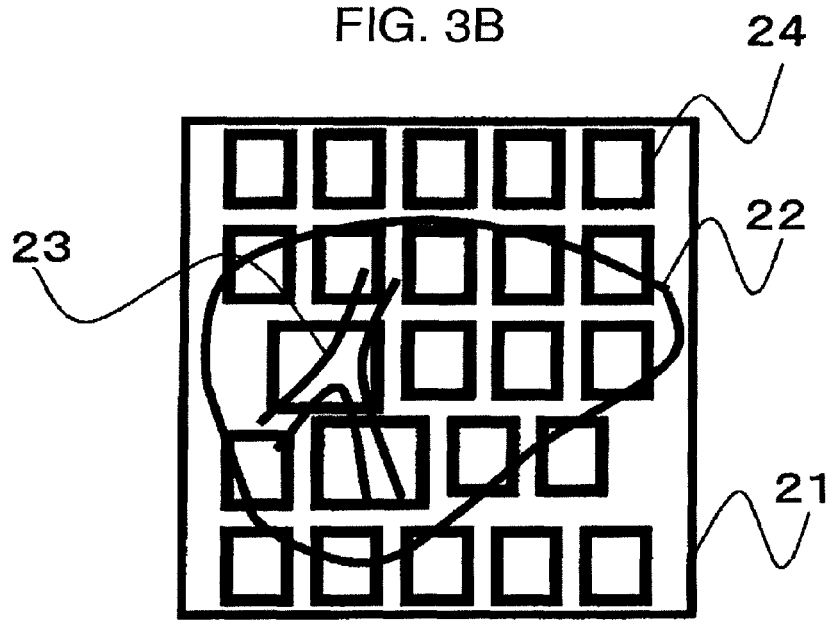
FIG. 3B is a drawing showing setting of a plurality of measuring areas, in a diagnostic imaging apparatus of the embodiment.

Then, explanation will be given on a method for setting measuring areas in the step 2, with reference to FIGS. 3A and 3B. In the present invention, a plurality of the measuring areas 24 are set in the ultrasonic images 21, and the most consistent area in each of the measuring areas is extracted from inside the next frame, by cross-correlation calculation or a least square method. By regarding movement inside each one of the measuring areas as rigid body movement not accompanying deformation, and by combining each of the movement determined in each of the measuring areas, deformation of a whole target object is measured.

As a signal component used in measurement, a contour component such as a contour of a target object or a boundary between tissues or the like, and a speckle component, which is formed by mutual interference of ultrasonic waves themselves scattered by minute scattering bodies present in a scattered way in a tissue inside or outside of the target object, is considered. In the present invention, both components are not differentiated in calculation of moving amounts by setting measuring areas throughout an image. Use of a speckle component is capable of measuring body movement in areas, where characteristic brightness information such as a tissue contour or the like is not obtained. Sizes of measuring areas change corresponding to a structure inside the area. In FIGS. 3A and 3B, the liver tissue 22 and the blood vessel structure 23 inside the liver tissue are shown, as examples. For areas not having a characteristic structural body, measuring areas having a size of about two times a speckle component are set, because such areas are constituted by a speckle component. Specific size thereof is about 2.5 mm in an azimuth direction and about 1 mm in a depth direction, under conditions of a probe diameter of about 40 mm, a frequency of 10 MHz, and an F-number of 1. For a position having a blood vessel structure, areas having a size in a degree sufficiently containing the structure thereof are set.

Figure 4:
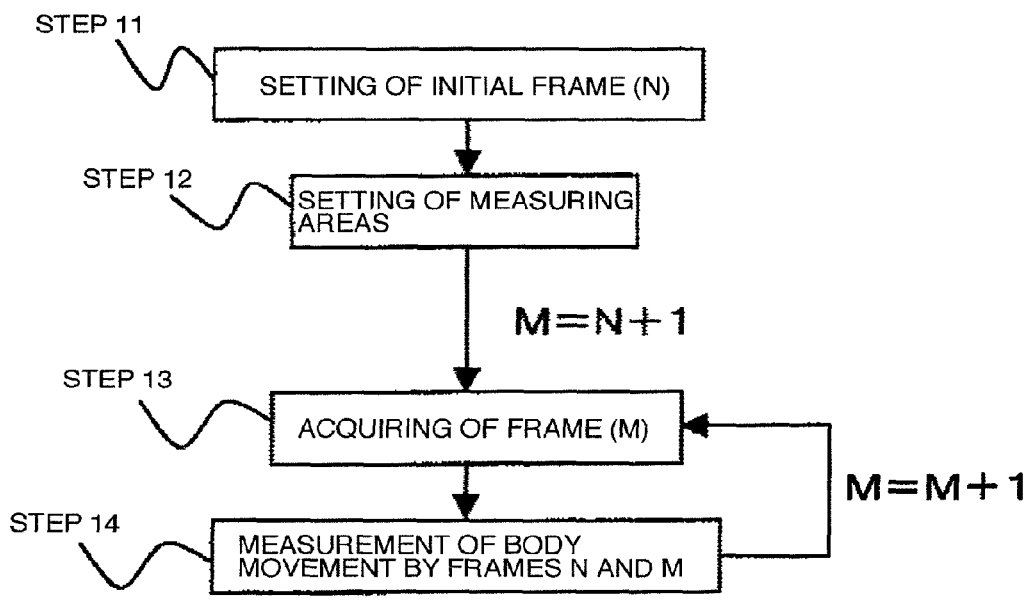
FIG. 4 is a flow chart explaining the step from measuring area setting to evaluation of body movement vectors, in a diagnostic imaging apparatus of the embodiment.
Figure 5:
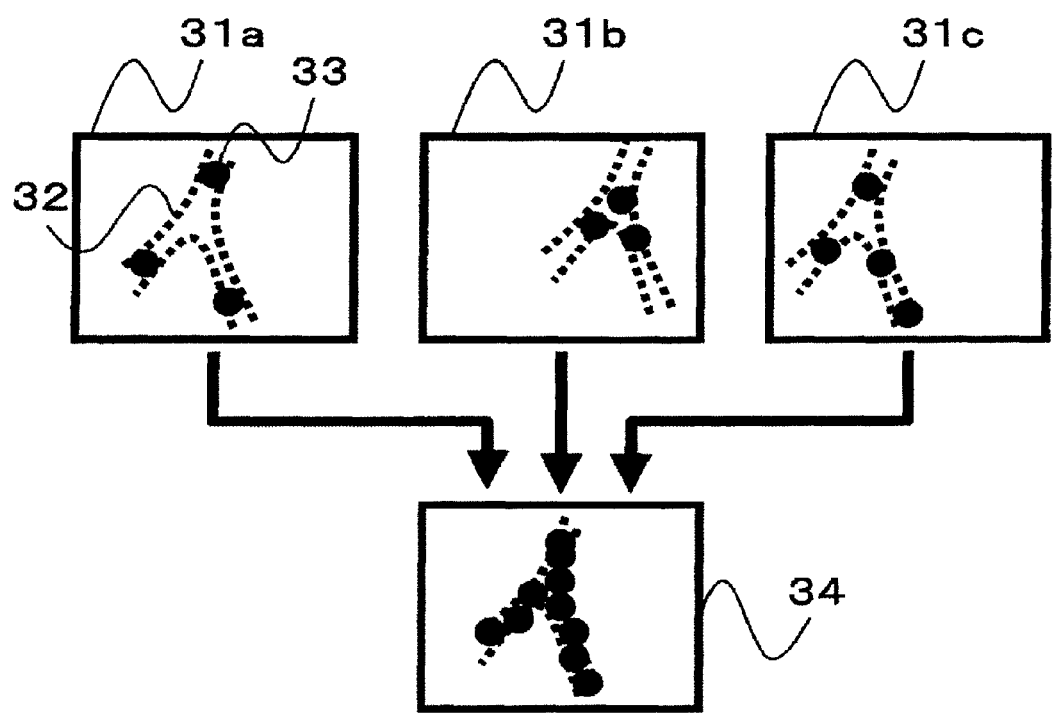
FIG. 5 is a drawing representing a method for extracting a blood vessel structure by a contrast medium signal, in a diagnostic imaging apparatus of the embodiment.

Then, explanation will be given on a method for measuring body movement of the step 3. FIG. 4 shows a flow chart for measurement of body movement in each of the measuring areas. First of all, a fundamental ultrasonic image frame (N) is acquired (the step 11), and an arbitrary number of measuring areas are set on this image (the step 12). Then, a time-series continuous next frame (M=N+1) is acquired (the step 13). A most consistent area on the frame M to the measuring areas, set on the frame N, is extracted by cross-correlation calculation or a least square method, and displacement thereof is measured as body movement (the step 14). Subsequently, by returning to the step 13, the next frame (M=N+2) is acquired to measure body movement by a similar method as in the above, using the frame N and the frame M (M=N+2). By repeating the step 13 and the step 14, body movement of a target object is measured from the frame N up to the desired frame number.

For measurement of body movement, cross-correlation calculation or a least square method is used, however, the optimal method differs depending on a signal component for carrying out measurement of body movement. In general, cross-correlation calculation has higher measurement sensitivity as compared with a least square method; therefore, in the case where change of a target signal component is large between frames for carrying out measurement of body movement, correct measurement becomes impossible. For example, in the case where an ultrasonic contrast medium is used, change of a signal component is large, because the contrast medium drastically moves about inside the measuring areas, therefore use of a least square method, which is not affected by small change of a signal component, is suitable. Explanation will be given below with reference to equations. For simplicity in explanation, one-dimensional model is assumed, and two images for carrying out measurement of body movement are represented as follows by $f_1(x)$ and $f_2(x)$:

$$f_1(x) = f(x) + n_1(x) \quad \text{(Expression 1)}$$
$$f_2(x) = f(x - \alpha_0) + n_2(x) + n_c(x)$$

wherein $n_1(x)$ and $n_2(x)$ represent noises on the images; $n_c(x)$ represents a signal of the contrast medium; and $\alpha_0$ represents location change by body movement. First of all, $C_1(\alpha)$ obtained by cross-correlation calculation is represented as follows:

$$C_1(\alpha) = \int f_1(x - \alpha) f_2(x) dx \quad \text{(Expression 2)}$$

$$= \int [f(x - \alpha) + n_1(x - \alpha)]$$

$$[f(x - \alpha_0) + n_2(x) + n_c(x)] dx$$

$$= \int f(x - \alpha) f(x - \alpha_0) dx +$$

$$\int f(x - \alpha) n_c(x) dx$$

Then, $C_2(\alpha)$ obtained by a least square calculation is represented as follows:

$$C_2(\alpha) = \left\{ \int [f_1(x-\alpha) - f_2(x)]^2 dx \right\}^{\frac{1}{2}} \quad \text{(Expression 3)}$$

$$= \left\{ \int [f(x-\alpha) + n_1(x-\alpha) - f(x-\alpha_0) - n_2(x) - n_c(x)]^2 dx \right\}^{\frac{1}{2}}$$

$$= \left[ \int f(x-\alpha)^2 + f(x-\alpha_0)^2 + n_1(x-\alpha)^2 + n_2(x)^2 + n_c(x)^2 - 2f(x-\alpha)f(x-\alpha_0) - 2f(x-\alpha)n_c(x) + 2f(x-\alpha_0)n_c(x) \right]^2 dx \right]^{\frac{1}{2}}$$

As for limit value of each of $C_1(\alpha)$ and $C_2(\alpha)$ for $\alpha \to \alpha_0$, the first term of $C_1(\alpha)$ is stable and reaches the maximal value, however, the second term does not necessarily take the maximal value. On the other hand, $C_2(\alpha)$, as limit value for $\alpha \to \alpha_0$, takes the minimal value, because the terms excluding from the third to the fifth terms converge to 0, and from the third to the fifth terms are stable not depending on $\alpha$. Namely, it means that in the case where a contrast medium signal is equivalent to or larger than f(x), measurement of body movement by a least square method can be carried out in high precision.

Figure 10:
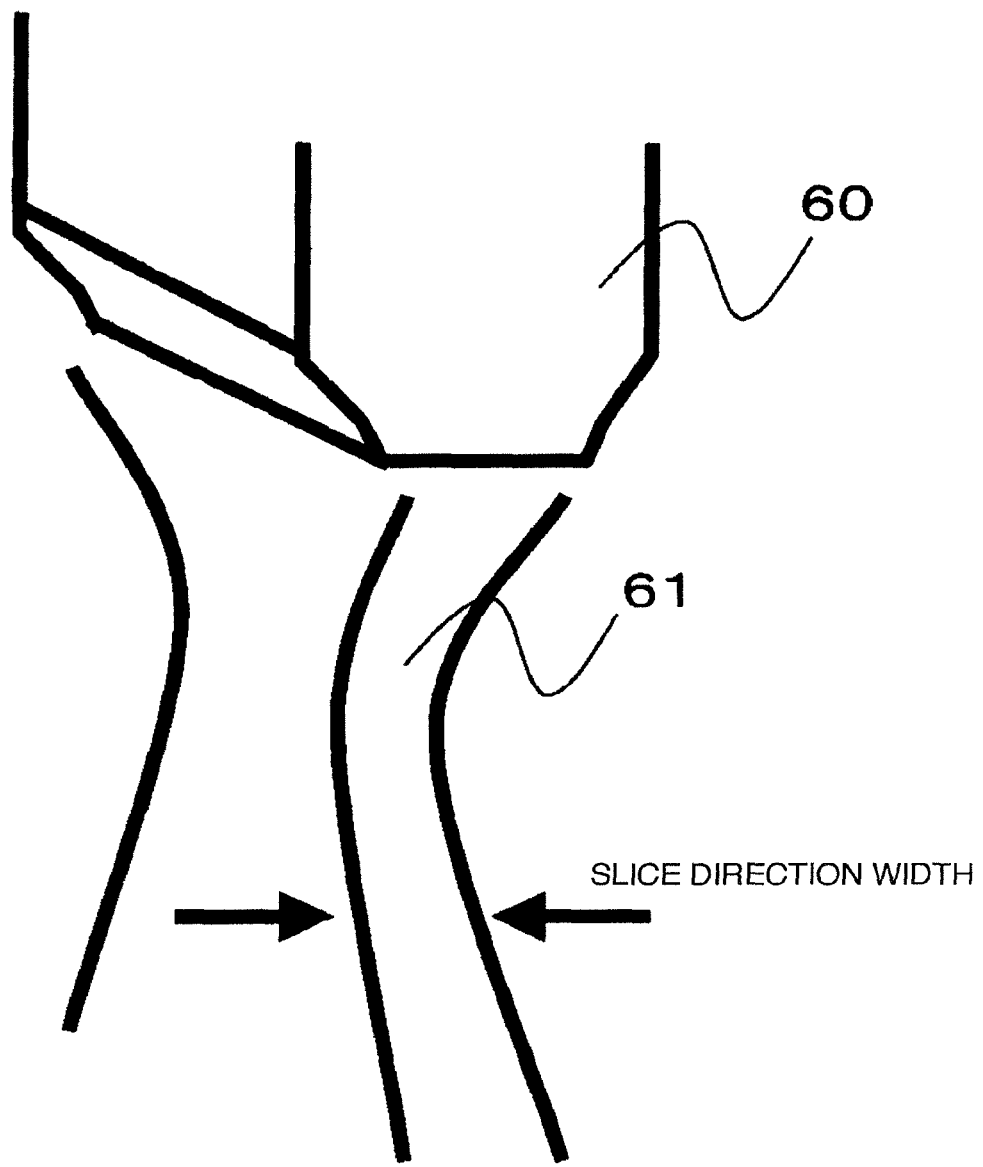
FIG. 10 is a drawing showing an ultrasonic probe and spatial spread of ultrasonic beams.

By setting a second ultrasonic probe orthogonal to an imaging plane (a first imaging plane) for measurement of body movement, more correct measurement of body movement and image accumulating (subtracting) processing become possible. In the case where measurement of body movement is carried out in the first imaging plane, and a target object moves mainly in a plane (a second imaging plane) orthogonal to the first imaging plane), brightness change of a target signal component is large and measurement precision in the first imaging plane is reduced. This measurement precision depends on slice direction width of the first imaging plane. As shown in FIG. 10, the ultrasonic beams 61 irradiated from the one-dimensional array ultrasonic probe 60 have special spread depending on diameter width, wavelength and depth of the ultrasonic probe. Here, beam spread in a slice direction is referred to as slice direction width.

Owing to this slice direction width, sensitivity sufficient to measurement can be obtained, which in turn makes possible measurement of body movement in the first imaging plane, even when the target object moves in a slice direction within a certain range. By an experiment using a phantom simulating a living body, as long as movement amount in the second imaging plane, between images for measuring body movement, is within about 20% of the slice direction width of the first imaging plane, measurement of body movement in the first imaging plane is possible in a precision of about a pixel size (from 10 to 100 μm) of a plane for measuring body movement; a typical example is about 0.4 μm, under conditions of a shorter axis diameter of the probe of about 10 mm, a frequency of 10 MHz, and an F-number of 1. In addition, in the case where movement of a target object are observed before inspection, and the ultrasonic probe is immobilized at a position so that movement in a slice direction is about 20% of the slice direction width, the second imaging plane is not necessarily set, in particular.

Then, explanation will be given on image accumulating or subtracting processing of the step 4. Whether images are accumulated or subtracted or used in combination of both, in extraction of change of a target object with time, depends of information to be extracted. Explanation will be given below on several examples thereof.

As an example where image accumulating is effective, there is a blood vessel extraction technology using an ultrasonic contrast medium. The ultrasonic contrast medium is a minute air bubble with a diameter of about several μms. Therefore, the ultrasonic contrast medium intermittently infiltrates into a fine blood vessel having a diameter of about the same level as compared with the ultrasonic contrast medium. In FIGS. 5, 31a, 31b, and 31c show ultrasonic images continuously acquired in time series. On each of the images, the blood vessel structure 32 not imaged practically, and the contrast medium 33 infiltrated along the blood vessel structure are shown. Spatial positional relation of the blood vessel structure 32 on each of the images is mutually displaced due to body movement of a target object. By correction of this body movement and by accumulating the ultrasonic images 31a, 31b, and 31c, the passing route of the ultrasonic contrast medium 33 is extracted and the accumulated imaged 34 is constituted, by which the blood vessel structure can be judged. For this accumulation processing, a B-mode image may be used, however, a contrast mode is particularly effective, where a contrast medium signal is highlighted. Furthermore, by body movement in a slice direction, effect that a three-dimensional structure of the blood vessel is drawn is also obtained. Because an imaging plane changes caused by body movement in a slice direction, three-dimensional information on a target object is included in an image data acquired. By subjecting these images to accumulating processing, a perspective image having width in a slice direction can be obtained, and a three-dimensional structure of the blood vessel can be imaged. In particular, in the case where the blood vessel usually meandering in a slice direction is imaged, it is drawn as a broken line on an image, however, by subjecting the image to accumulating processing, a line structure as the blood vessel can be drawn on an image, thanks to effect of the perspective image.

Figure 6:
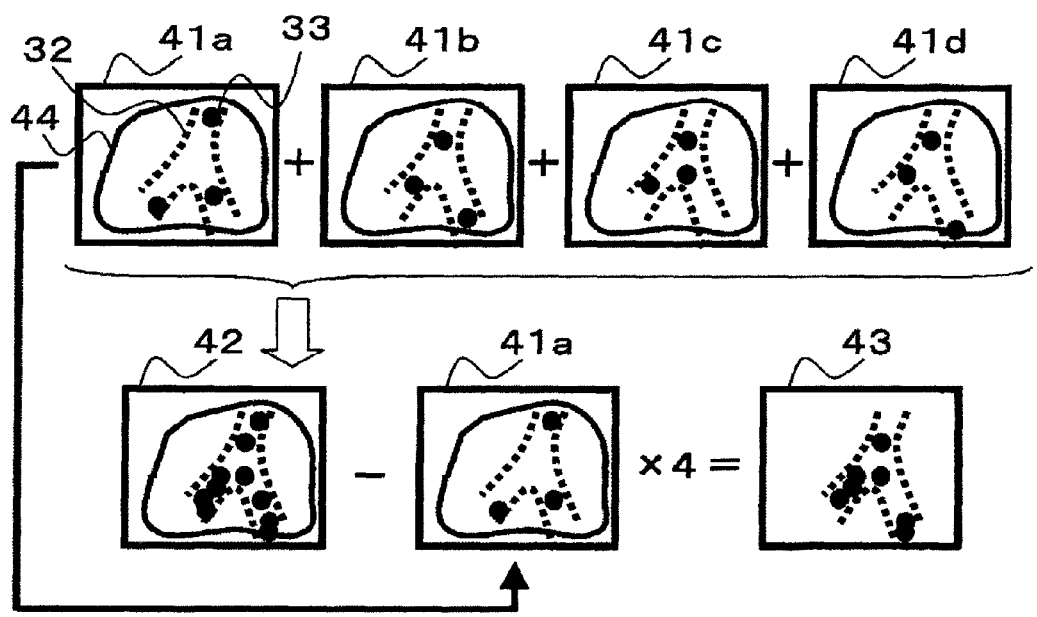
FIG. 6 is a drawing representing a method for removing a signal of other than a blood vessel structure, in a diagnostic imaging apparatus of the embodiment.

In addition, by removing signal components (tissue components) other than a blood vessel structure of a target object, a far clearer blood vessel structure can be drawn. A plurality of methods for removing tissue components is considered. The first method thereof is a method for sequentially constituting units, which are constituted by several or several tens pieces of images, while acquiring images, in the image accumulating process, to remove background in each of the units. Explanation will be given on the case where image number constituting a unit is 4 pieces, with reference to FIG. 6. Images are designated as 41a, 41b, 41c and 41d, in the order of acquiring the images. Each of the images contains the structure component 44 not changing with time. Then, the image 41a acquired first is set as a background image. Here, the image acquired first in the unit was set as a background image, however, any of 41b, 41c and 41d may be selected. Next, the accumulated image 42 is constituted by accumulating the images 41a, 41b, 41c and 41d constituting the unit, and the background image 41a is subtracted by number of pieces that constitutes the unit.

As a result, the image 43 can be constituted, wherein only a contrast medium signal changing with time is extracted. The second method is a method for noticing one pixel constituting an image. In one pixel corresponding to a blood vessel structure, large difference in brightness level is generated before and after the contrast medium passes. On the other hand, because a tissue component little changes with time, the above difference in brightness level is not generated therein. By utilization of this nature, the tissue component can be removed. Similarly as in the first method, a unit is constituted by plural pieces of images. Then, by sequential comparison of pixels themselves at the same position, as for images in a unit acquired, images constituted by maximal value and minimal value in each of the pixels are drawn. The image with the maximal value corresponds to a contrast medium signal, and the image with the minimal value corresponds to a tissue component. Therefore, by subtracting the image with the minimal value from the image with the maximal value, a tissue component can be removed.

By carrying out similar accumulating processing using a B-mode image, an image with higher contrast resolution as compared with an image not subjected to accumulating processing can be acquired. The principle thereof resides mainly in the following two points. One is reduction of electric noise. A signal received to constitute a B-mode image contains, in addition to a signal steadily acquired, such as a tissue echo, electric noise that randomly generates. Accumulating processing by adding correction of body movement highlights a signal steadily received from a specific position, therefore increases a dynamic range of an image. As a result, a randomly generating signal irrespective of a position provides low brightness on an image, and thus enhances contrast resolution. In addition, in the case where a target object is a blood vessel, a random signal from a reflection source flowing in a blood vessel is removed, while a stationary structural body is drawn in high contrast. Therefore, it is also useful to an application in diagnosing a position of blood vessel infarct caused by blood clot or the like. Another one is compound effect in a slice direction. This effect is generated by body movement in a slice direction, as already explained in blood vessel drawing technology by an ultrasonic contrast medium. By body movement in a slice direction, ultrasonic waves are irradiated in multiple stages substantially in a slice direction, and effect of highlighting tissue contour or removing a speckle component can be obtained.

Figure 11:
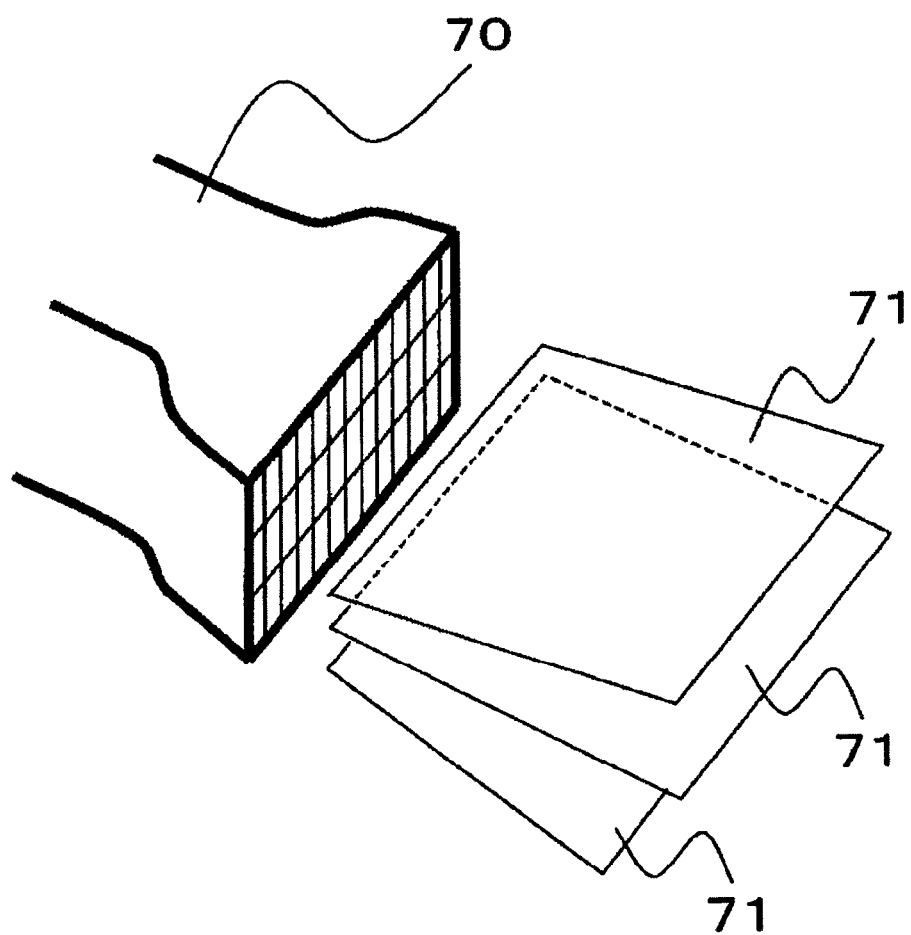
FIG. 11 shows a two-dimensional array probe and imaging plane scanning in a slice direction.

In image accumulating technology explained above, body movement in a slice direction are not elements to reduce measurement sensitivity of body movement in an imaging plane to be accumulated, but provide effective action such as rendering effect or compound effect. To utilize this effect to a maximum extent, it is necessary to widen ultrasonic transmitting beams in a slice direction, or to move an imaging plane mechanically or electronically. The former method not only deteriorates spatial resolution of each of the images to be accumulated, but also causes reduction of measurement sensitivity of body movement, therefore, the latter method is a practical method. FIG. 11 shows an example of the two-dimensional array ultrasonic probe 70 to provide an electronically oblique imaging plane in a slice direction. In each of the imaging planes 71, beams in a slice direction are focused by an acoustic lens, which is equipped with in an ultrasonic probe. Because the oblique of the imaging plane in a slice direction is about several mms, less channel number in a slice direction is enough as compared with an azimuth direction. In this case, phase delay processing considering effect of the acoustic lens is required. In the case where the channels in a slice direction are arranged in such number as providing nearly equivalent effect as the acoustic lens, the acoustic lens is not required. As a result, effect of a perspective image or compound effect can be obtained even in a target with small body movement in a slice direction.

Figure 7A:
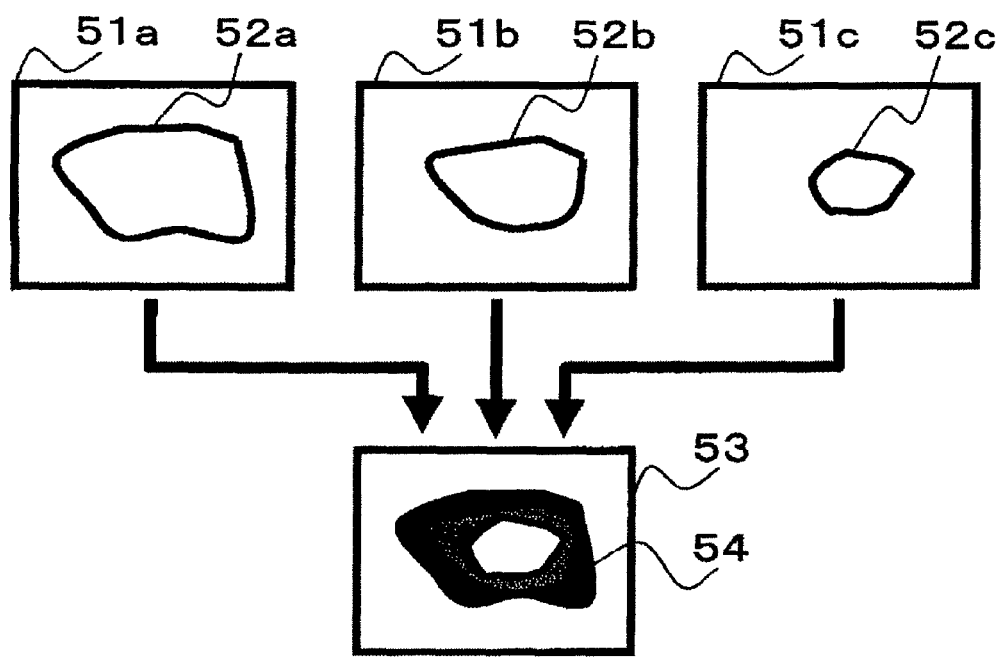
FIG. 7A is a drawing representing imaging of tissue form change by subtracting processing, in a diagnostic imaging apparatus of the embodiment.
Figure 7B:
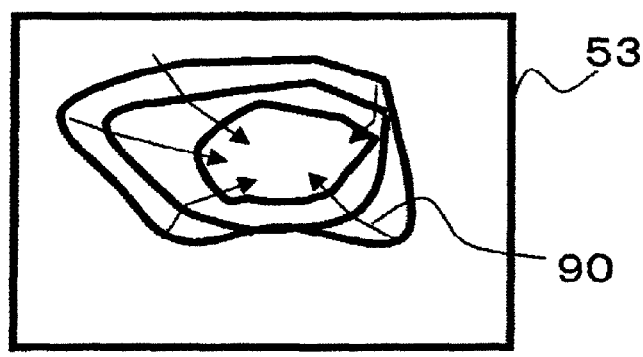
FIG. 7B is a drawing representing imaging of tissue form change by subtracting processing, in a diagnostic imaging apparatus of the embodiment.

Next, as an example of image subtracting, there is an imaging of form change such as form change of cancer or tissue degeneration in less invasive therapy. Explanation will be given with reference to FIGS. 7A and 7B. The steps from image acquiring to image subtracting processing are as shown in FIG. 2, and are similar as in the above-described blood vessel structure drawing by an ultrasonic contrast medium. Images after measurement of body movement are designated as 51a, 51b, and 51c of FIG. 7A, in the order of time-series. Target tissue is shown as 52a, 52b, and 52c on each of the images. By subtracting processing among each of the images themselves, tissue form change generated among the images can be imaged (FIG. 7B, the subtracting processed image 53). Furthermore, by showing this change by color gradation (FIG. 7A, the gradation processed image 54), form change of the target tissue can be displayed as an accurate and objective image. In addition, such a display embodiment is also considered that the form change is displayed like contour lines, and change process is shown by the vector 90. As a result, not only total size but also local form change processes can be displayed.

Figure 8:
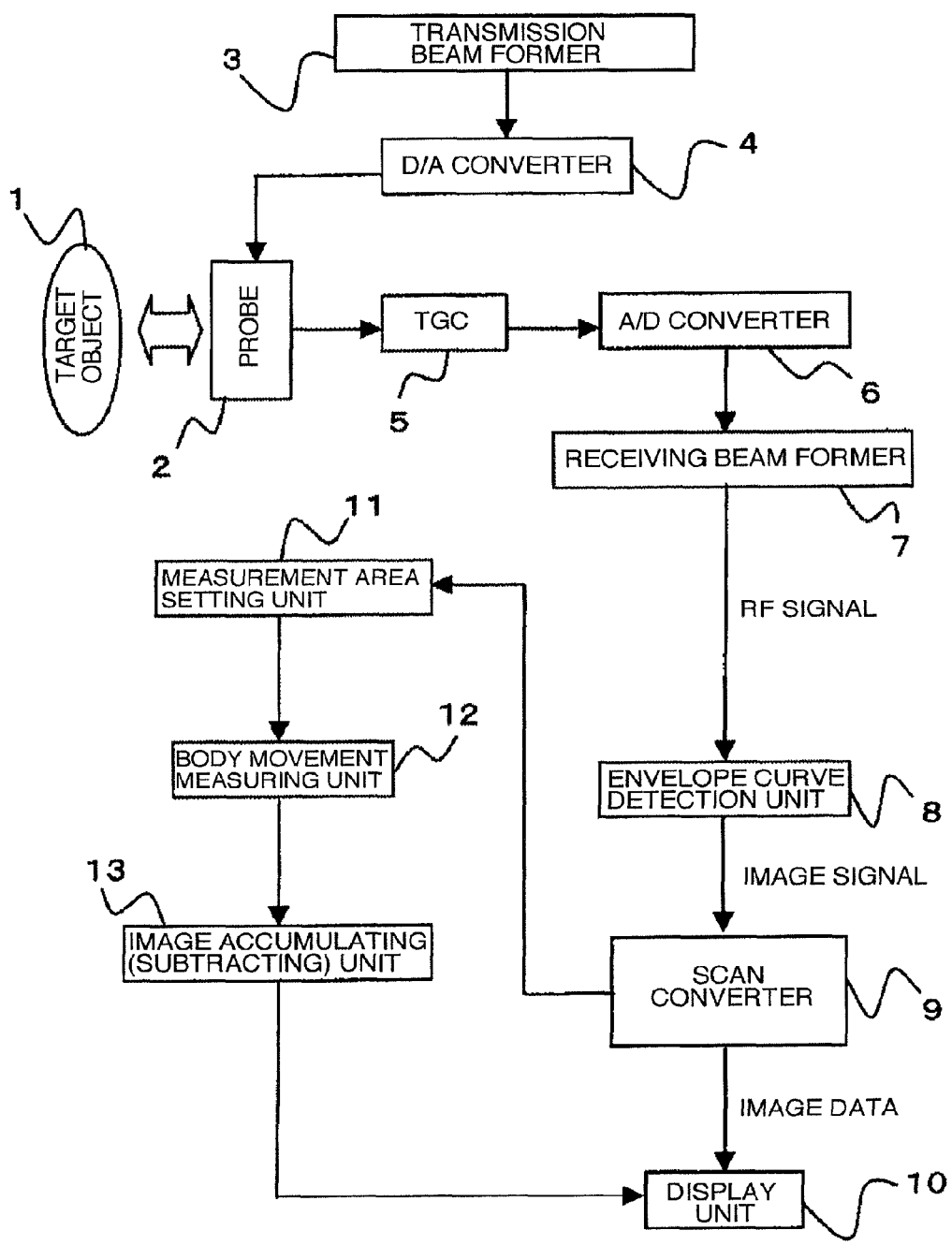
FIG. 8 is a block diagram in the case where measurement of body movement and image accumulating (subtracting) processing are carried out by a data from a scan converter, in a diagnostic imaging apparatus of the embodiment.
Figure 9:
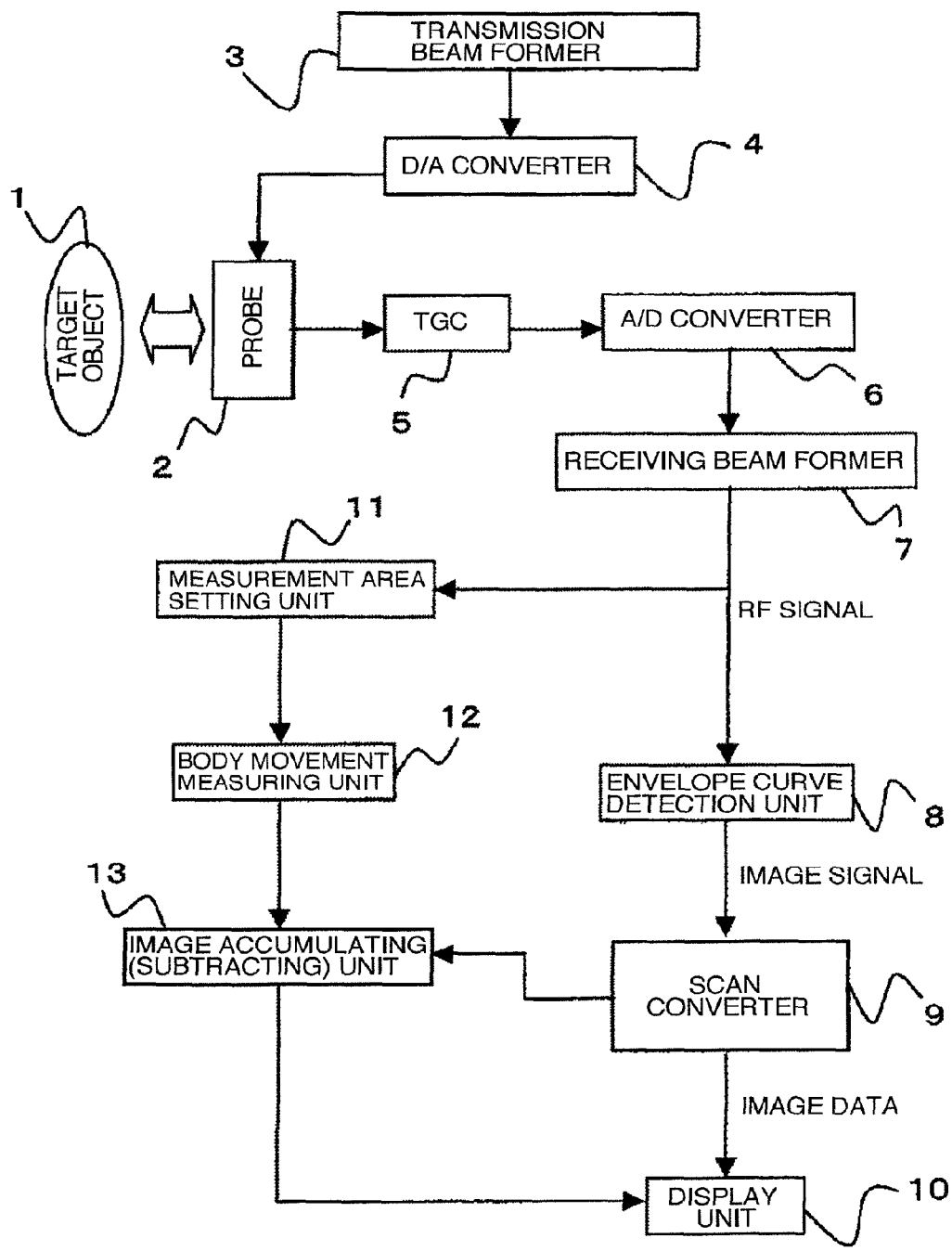
FIG. 9 is a block diagram in the case where measurement of body movement is carried out by an RF data, and image accumulating (subtracting) processing is carried out by a data from a scan converter, in a diagnostic imaging apparatus of the embodiment.

As shown in a block diagram of FIG. 1, measurement of body movement and image accumulating (subtracting) processing used an RF data, however, other than this, as shown in FIG. 8, measurement of body movement and image accumulating (subtracting) process can be carried out using an image data from the scan converter 9. In addition, as shown in FIG. 9, the measurement of body movement may use an RF data, and the accumulating (subtracting) processing may use the image data from the scan converter 9.

The present invention is applicable also in a pulse inversion mode. The pulse inversion mode is, as explained in the section of "Background Art", a method for acquiring higher harmonic wave components in high S/N ratio, by continuous irradiation of a fundamental wave and a reversed phase wave, and accumulating reflecting waves of both. By accumulating processing, only fundamental wave components disappear and higher harmonic wave components double. On the other hand, by subtraction processing, only fundamental wave components are left and higher harmonic wave components disappear. Therefore, by the above-described accumulating processing, a highlighted image of a contrast medium (a contrast medium image), which is a higher harmonic wave component, can be constituted, and on the contrary, by the subtracting processing, an image of only a tissue component (a tissue image), wherein higher harmonic wave components are removed, can be obtained. As a result, by carrying out measurement of body movement by the tissue image, wherein signal change is moderate, and by carrying out accumulating (subtracting) processing by the contrast medium image, image accumulating by high-precision correction of body movement can be realized, and an image, wherein a blood vessel structure is extracted, can be displayed.

Figure 12:
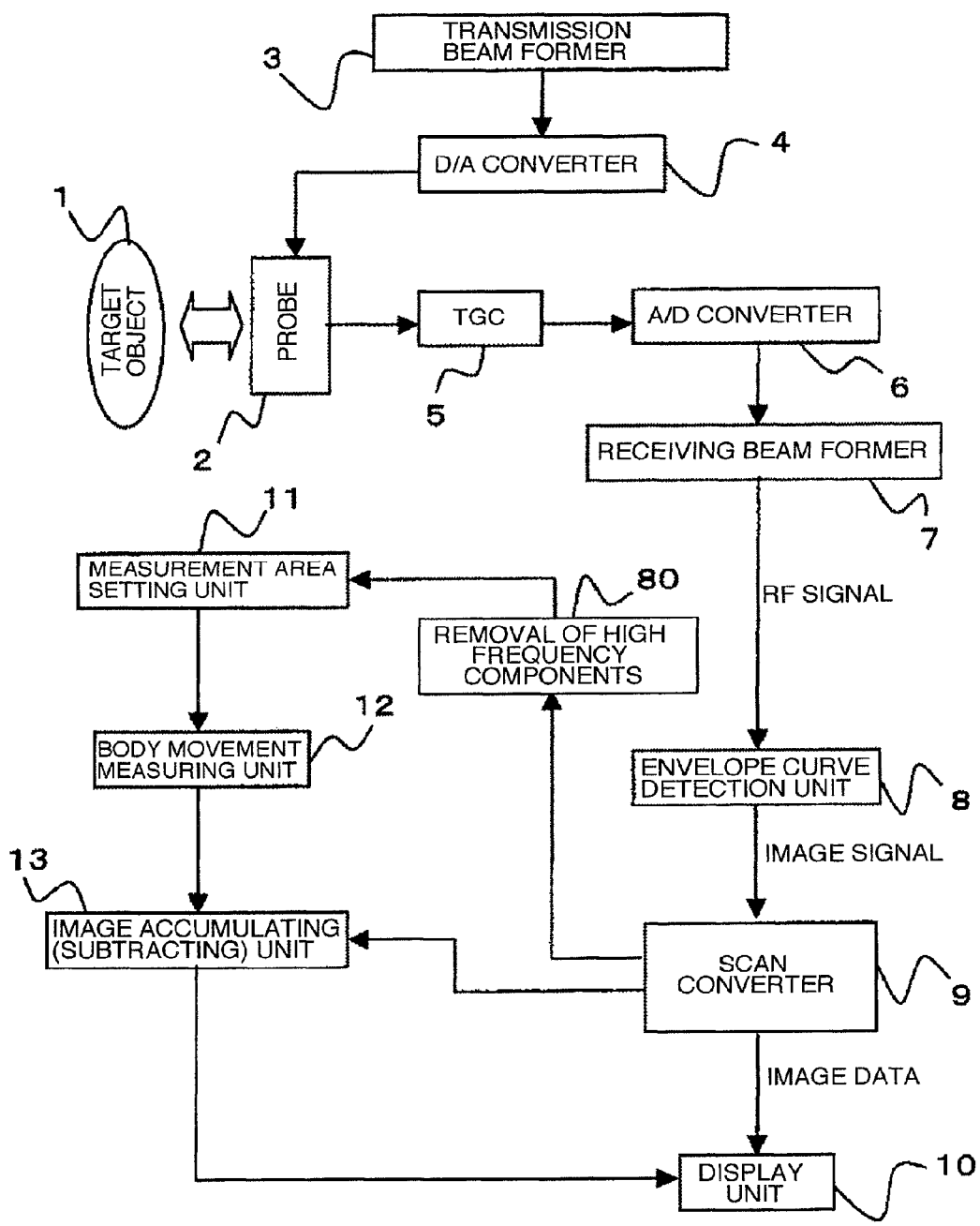
FIG. 12 is a block diagram in the case where measurement of body movement is carried out by images that are obtained by subjecting a data from a scan converter to removing processing of high frequency components, and accumulating (subtracting) processing is carried out by images not subjected to removing processing of high frequency components, in a diagnostic imaging apparatus of the embodiment.
Figure 13:
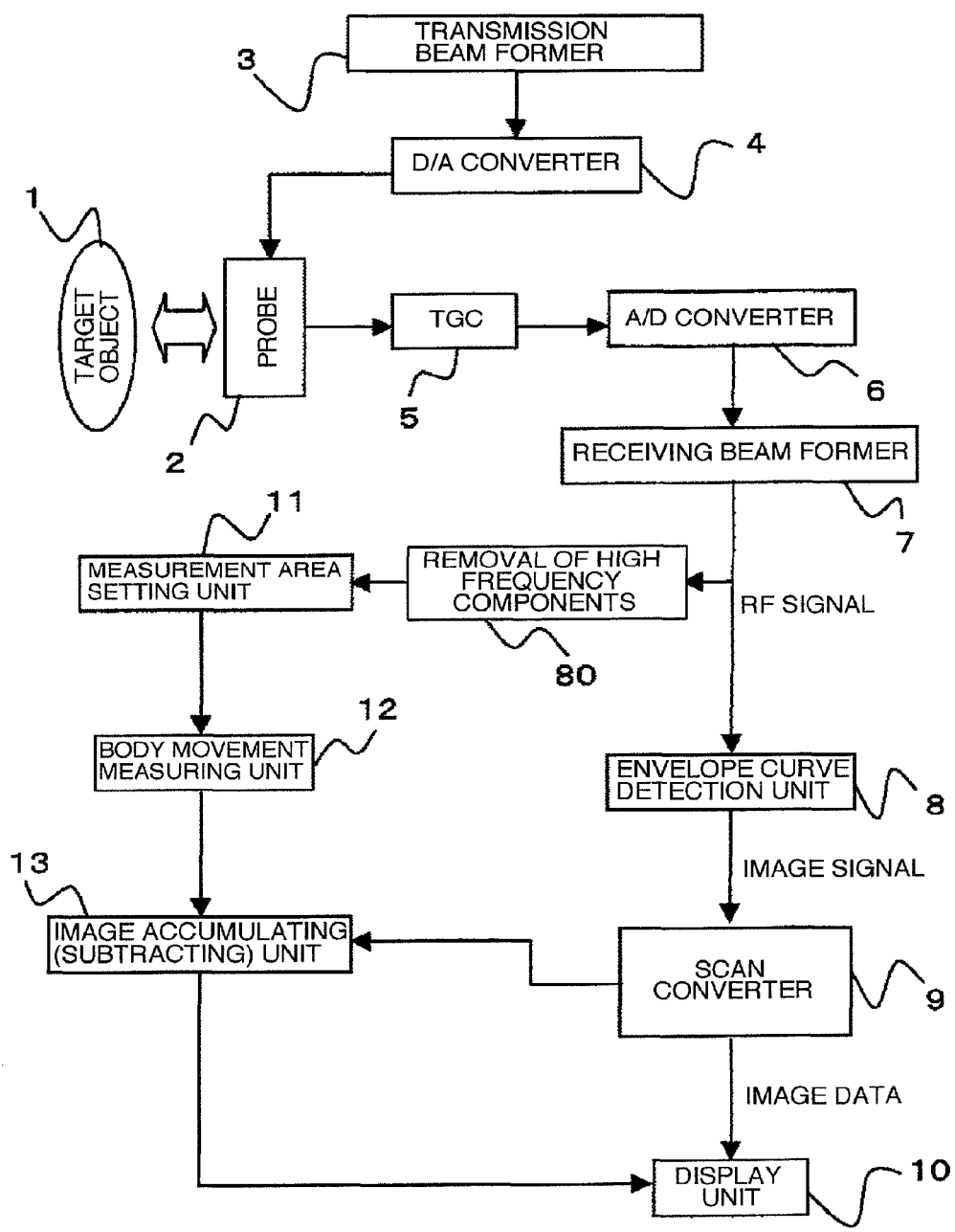
FIG. 13 is a block diagram in the case where measurement of body movement is carried out by images that are obtained by subjecting an RF data to removing processing of high frequency components, and accumulating (subtracting) processing is carried out by images from a scan converter, in a diagnostic imaging apparatus of the embodiment.

In addition, there is such a method that, by carrying out measurement of body movement by an image, wherein high frequency components such as electric noise or a contrast medium signal are removed, and accumulating (subtracting) processing is carried out by an image not being subjected to filter processing. For example, in a block diagram of FIG. 12, an image data is sent from the scan converter 9 to the high frequency component removing unit 80 and the image accumulating (subtracting) unit 13. Alternatively, as shown in a block diagram of FIG. 13, the RF data is sent to the high frequency component removing unit 80 to carry out measurement of body movement. It is a method for using images from the scan converter 9, as for the image accumulating (subtracting) processing based on a result of measurement of body movement.

Explanation will be given below on embodiments of the present invention. Time required in image display is mainly determined by the following two elements: one is an acquiring time of images to be accumulated, and the other is time required in accumulating processing. As for the acquiring time of images, it is determined by number of pieces to be acquired and frame rate to be set, and requires from two to three seconds. Therefore, an accumulated image displayed first is an image acquired several seconds before. As for an accumulated image to be displayed next, image display in real time becomes possible, by reading an image, wherein the first frame is removed from an already acquired image data, at each time of acquiring one frame, and then by adding the acquired image to be subjected to accumulating processing.

Therefore, an operator carries out screening of a target object by a B-mode, and moderates movement of a probe at a desired position, to enable an embodiment for carrying out automatic accumulating processing. The above description was given on embodiments, however, the present invention should not be limited thereto, and it is apparent to those skilled in the art that various modifications and corrections are possible within a range of the spirit and accompanied claims of the present invention.

The invention claimed is:

1. A diagnostic imaging apparatus comprising:
an ultrasonic probe which transmits ultrasonic waves to a target object and acquires a reflection signal from said target object, for a plurality of image frames which is constituted as two-dimensional ultrasonic image acquired by said ultrasonic probe;
a measuring area setting unit which sets, for each image frame, a plurality of measuring areas used for measuring a body movement of said target object, and divides said two-dimensional ultrasonic image into said plurality of measuring areas;
a body movement measuring unit which measures body movement and deformation amounts of said target object, in comparison between said measuring areas of a base image frame and said measuring areas of following image frames which follow said base frame in time series;
an image accumulating/subtracting unit which accumulates or subtracts a plurality of images of the plurality of said image frames after a body movement correction based on said measurement of said body movement; and
an image display unit which displays a reconstructed two-dimensional tomogram image processed by said image accumulating/subtracting unit by using said measuring areas; and
wherein, in a pulse inversion mode a higher harmonic wave component is acquired in high S/N ratio by continuous irradiation of a fundamental wave and a reversed phase wave, and by accumulating reflection waves of both, a display image is constituted by carrying out body movement measurement by the wave component obtained by accumulating/subtracting said reflection waves,
wherein the measuring area setting unit, the body movement measuring unit, the image accumulating/subtracting unit and the image display unit are at least partially embodied by one or more hardware component.

2. The diagnostic imaging apparatus according to claim 1, wherein the display image is constituted by carrying out body movement measurement by the fundamental wave component obtained by subtracting said reflection waves.

3. The diagnostic imaging apparatus according to claim 1, wherein the display image is constituted by carrying out body movement measurement by the higher harmonic wave component obtained by accumulating said reflection waves.

4. The diagnostic imaging apparatus according to claim 1, wherein the display image is constituted by subjecting to image accumulating processing using a higher harmonic wave component.

5. The diagnostic imaging apparatus according to claim 1, wherein the display image is constituted by subjecting to image subtracting processing using a higher harmonic wave component.

6. The diagnostic imaging apparatus according to claim 1, wherein there are a plurality of following image frames which are compared with the base image frame.

* * * * *